United States Patent [19]

Day et al.

[11] Patent Number: 5,384,421
[45] Date of Patent: Jan. 24, 1995

[54] PROCESS FOR MAKING SODIUM ACYLISETHIONATES

[75] Inventors: James F. Day, Charlotte, N.C.; Wolf-Dieter Mueller, Hofheim, Germany; Rainer H. R. Muth, Charlotte, N.C.

[73] Assignee: Hoechst Celanese Corporation, Somerville, N.J.

[21] Appl. No.: 934,062

[22] Filed: Aug. 21, 1992

[51] Int. Cl.⁶ .......................................... C07C 303/32
[52] U.S. Cl. ........................................ 554/92; 554/90; 554/88
[58] Field of Search .................................... 554/92

[56] References Cited

U.S. PATENT DOCUMENTS

| | | | |
|---|---|---|---|
| 2,635,103 | 4/1953 | Molteni et al. | 554/92 |
| 2,857,370 | 10/1958 | Sundberg | 530/213 |
| 2,923,724 | 2/1960 | Anderson et al. | 554/92 |
| 3,004,049 | 10/1961 | Schenck | 554/92 |
| 3,029,264 | 4/1962 | van Alphen et al. | 554/92 |
| 3,167,570 | 1/1965 | Bohunek | 554/91 |
| 3,320,292 | 5/1967 | Cahn et al. | 554/92 |
| 3,383,395 | 5/1968 | Cahn et al. | 554/92 |
| 3,394,155 | 7/1968 | Cahn et al. | 554/92 |
| 3,420,358 | 1/1969 | McCrimlisk | 554/92 |
| 3,420,857 | 1/1969 | Holland et al. | 554/92 |
| 3,429,136 | 2/1969 | Holt et al. | 62/114 |
| 3,745,181 | 7/1973 | Wrigley et al. | 554/49 |
| 4,100,097 | 6/1978 | O'Roark | 252/145 |
| 4,151,105 | 4/1979 | O'Roark | 252/145 |
| 4,405,526 | 9/1983 | Lamberti et al. | 260/400 |
| 4,515,721 | 5/1985 | Login et al. | 554/92 |
| 4,536,338 | 8/1985 | Urban et al. | 554/92 |
| 5,185,101 | 2/1993 | Welpert | 252/554 |
| 5,300,665 | 4/1994 | Tracy et al. | 554/49 |

FOREIGN PATENT DOCUMENTS

| | | |
|---|---|---|
| 0067624 | 3/1982 | European Pat. Off. |
| 3442579 | 11/1984 | Germany. |
| 3616843 | 5/1986 | Germany. |
| 848463 | 5/1957 | United Kingdom. |
| 853590 | 11/1960 | United Kingdom. |
| 869744 | 6/1961 | United Kingdom. |
| 917952 | 2/1963 | United Kingdom. |

OTHER PUBLICATIONS

American Society for Testing and Manufacturing standard D-156 (ASTM Designation D 156-87), Standard Test Method for Saybolt Color of Petroleum Products (Saybolt Chromometer Method), pages 96-100, 1987.

Synthetic Detergents (7th Edition), by A.S. Davidsohn and C. Milwidsky, pages 247-248, 1987.

Epton, S.R., "Method of Analysis for Certain Surface Active Agents", Nature, Volume 160, pages 795-796 (1947).

Detergent Analysis-A Handbook for Cost-Effective Quality Control, by B.M. Milwidsky and D.M. Gabriel (George Goodwin, London 1982), pages 119-121, 132-135, 254-255 and 198-199.

American Society for Testing and Manufacturing standard D-445-88, Standard Test Method for Kinematic Viscosity of Transparent and Opaque Liquids (and the Calculation of Dynamic Viscosity), pages 154-159, 1988.

Hawley's Condensed Chemical Dictionary (9th Edition 1987), page 873, 1986 by Hawley, Gessner G.

Primary Examiner—José G. Dees
Assistant Examiner—Dwayne C. Jones
Attorney, Agent, or Firm—Rosemary M. Miano

[57] ABSTRACT

This invention discloses an improved method for making salts of acylisethionates using a direct esterification of a fatty acid with one or more salts of a selected hydroxyalkanesulfonic acid in the presence of a catalyst selected from the described group. This method may be used at temperatures below 200 degrees C.

13 Claims, No Drawings

PROCESS FOR MAKING SODIUM ACYLISETHIONATES

BACKGROUND OF THE INVENTION

This invention relates to the preparation of esters of fatty acids with hydroxyalkyl sulfonates, some of which are also known as isethionates. These compounds are well known as valuable synthetic lime soap dispersants and detergents, wetting agents and materials which are particularly useful in the manufacture of toilet soaps.

A variety of ways of making these compounds has been described in the art. U.S. Pat. No. 3,420,857 to Holland et al. and U.S. Pat. No. 3,420,858 to McCrimlisk disclose methods for the formation of fatty esters of hydroxysulfonates to obtain products which have reduced amounts of esters of higher molecular weight fatty acids and unreacted lower molecular weight fatty acids. The methods comprise continuously supplying to the reaction vessel, fatty acid reactants of a composition corresponding to fatty acids volatilized during the course of the reaction (in order to reduce the proportion of esters of relatively higher molecular weight fatty acids) and utilizing an improved stripping process to reduce the lower molecular weight fatty acid content. The method includes heating a mixture of an hydroxyalkylsulfonate and fatty acids to a temperature between about 390 degrees F. and 500 degrees F. (about 199–260 degrees C.). The examples are run at temperatures of at least 450 degrees F. (about 232 degrees C.). These patents note that temperatures below 450 degrees F. significantly reduce reaction rates. These patents also list a number of reaction promoters for the direct esterification reaction, including salts of strong acids and weak bases, zinc oxide and magnesium oxide, and acids and acid formers.

U.S. Pat. No. 3,429,136 to Holt et al. discloses a method for making esters of hydroxysulfonates in which the hot hydroxy-sulfonate esters are cooled from temperatures on the order of 350 degrees F. to 500 degrees F. (about 177–260 degrees C.), which are encountered in the preparation of such compounds, to a temperature below about 330 degrees F. (about 165.6 degrees C.). At this point the reaction is quenched by injecting cold water. The patent states that this quenching method is carried out without detectable amounts of hydrolysis.

U.S. Pat. No. 3,745,181 to Wrigley et al. discloses the preparation of 2-sulfoethyl esters of a number of fatty acids by acylating the sodium isethionate with the corresponding isopropenyl fatty ester by a transesterification reaction. The patent states that high purity products may be obtained using reaction times of 10–90 minutes and temperatures from 125–200 degrees C. Examples run at less than 200 degrees C., however, seem to result in decreased yields.

U.S. Pat. No. 4,405,526 to Lamberti et al. discloses a method for producing directly esterified fatty acylisethionates having a yellowness index less than about 6.0. The process consists essentially of reacting a fatty acid with an alkali metal isethionate in the presence of a catalyst comprising a mixture of zinc oxide (ZnO) and an organic sulfonic acid wherein the molar ratio of ZnO to organic sulfonic acid is about 1:1.7 or less and heating the reaction at about 200 degrees C. to about 225 degrees C. until the desired product is formed.

U.S. Pat. No. 4,515,721 to Login et al. discloses a process for the production of fatty acid esters of hydroxyalkyl sulfonate salts wherein the method comprises a) heating an excess of the fatty acids with the sulfonate until the water of condensation is removed; b) quenching the crude ester by immersion in an excess of cooled liquid in which the ester product is insoluble but in which unreacted, excess fatty acids are soluble; and c) filtering the slurry to separate the relatively pure ester. Isopropanol is taught as the preferred quenching liquid, but fatty alcohols (such as stearyl alcohol), fatty alcohol ethoxylates, polyethyleneglycols, fatty triglycerides (such as tallow or hydrogenated tallow), fatty esters and paraffins may also be used as the quenching liquid. The patent notes that the presence of a certain amount of such quenching liquids is acceptable and may actually facilitate detergent formulations. The method of this patent recites a temperature range of 200–250 degrees C., but all of the examples appear to be run at 250 degrees C.

U.S. Pat. No. 4,536,338 to Urban et al. discloses a method for preparing fatty acid isethionate soaps through direct esterification wherein the catalyst is quenched by an alkaline compound at the end of the esterification to inhibit transesterification between isethionate and later added stearic acids. The method comprises a) heating a mixture of $C_6$–$C_{19}$ monocarboxylic acids with an hydroxysulfonate in the presence of a catalyst such as acidified zinc oxide, strong acids or soluble zinc salts; b) removing the liberated water; c) quenching the catalyst with an alkaline compound; and d) adding a higher molecular weight $C_{15}$–$C_{24}$ fatty acid to the reaction mixture. The patent recites a reaction temperature of between 200 degrees C. and 260 degrees C. with 233 degrees C. being standard. The patent also mentions that increasing levels of zinc oxide to achieve faster rates of reaction gives a gritty feel to toilet bars made with the material.

German patent applications numbers 34 42 579 and 36 16 843 disclose a process for the esterification of carboxylic acids (RCOOH) with salts of hydroxyalkanesulfonic acids, wherein the R group of the acid is a saturated and/or unsaturated hydrocarbon of 7 to 31 carbons and the esterification takes place in the presence of a consistency regulator (such as paraffin) with a salt of the formula HO—$(CH_2)_n$—$SO_3X$, where n is a number from 2–4 and X is an alkali metal or ammonium cation ($NH_4^+$). The 34 42 579 application states that the esterification is preferably carried out in a vacuum at temperatures of about 220–245 degrees C., particularly 225–235 degrees C.

The synthesis of one type of compound of this class, fatty acid esters of sodium acylisethionate, may be generally represented as follows:

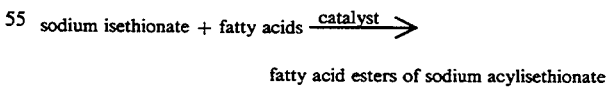

fatty acid esters of sodium acylisethionate

The sodium isethionate (also called sodium hydroxyethane sulfonate) may be made by reacting ethylene oxide and sodium bisulfite.

While there have been a number of attempts at developing improved processes for making fatty acid esters of hydroxyalkyl sulfonates, there still remains a need for having a process that uses a direct esterification of salts of an hydroxyalkanesulfonic acid but that can be practiced at reduced temperatures, such as below 200 degrees C., without substantial reduction in yields or reaction rates. There also remains a need for producing fatty acid esters of hydroxysulfonates which have reduced problems with odor and color and which do not produce bars having a gritty feel when used to make toilet bars (or produce bars with reduced gritty feel).

Thus, it is an object of this invention to provide a process for the manufacture of fatty acid esters of hydroxyalkane sulfonates, which process may conveniently be run at temperatures not exceeding 200 degrees C. without substantial loss in yield or reduction in reaction rates. It is also an object of this invention to provide such a process with appreciable savings in energy costs compared to processes run at higher temperatures. It is another object of this invention to provide a process which produces fatty acid esters of hydroxyalkanesulfonates which have reduced odor and color problems, especially when the material is blended to make toilet bars. It is a further object of this invention to provide a process which produces fatty acid esters of hydroxyalkanesulfonates which have desirable lathering properties and reduced gritty feel when used to make toilet bars. These and other objects of the invention will be apparent from the following description.

SUMMARY OF THE INVENTION

This invention comprises a method for making salts of acylisethionates of Formula I:

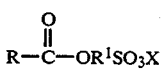

(I)

wherein:
R may be a saturated or unsaturated straight chain or branched hydrocarbyl group (preferably straight chain) from about 5 to about 31 carbons, such as 5-17 carbons;
$R^1$ is a saturated or unsaturated straight chain hydrocarbyl group having 2, 3 or 4 carbons, preferably 2 carbons; and
X is sodium, potassium, lithium or ammonium, and preferably sodium or potassium.

For purposes of this invention, the term "hydrocarbyl group" is herein defined as an alkyl, alkenyl or alkynyl group (or alkylene, alkenylene or alkynylene if the substituent has two bonds), consisting of hydrogen and carbon and having the number of carbons specified for the substituent being defined. In the case where the hydrocarbyl group is unsaturated, this will mean that there is one unsaturation and that unsaturation may occur anywhere in the group.

The method comprises a direct esterification of one or more fatty acids of Formula II: RCOOH, where R has the same definition as defined for Formula I, with one or more salts of hydroxyalkanesulfonic acids of Formula III: $HOR^1SO_3X$ (also called herein hydroxyalkanesulfonic acid salt), where $R^1$ and X have the values defined above.

The direct esterification may be done at a temperature between about 180 degrees C. and 240 degrees C. (but preferably at a temperature below 200 degrees C.), in the presence of a catalyst selected from the group consisting of selected alkane and hydroxyalkanesulfonic acids, aryl sulfonic acids, inorganic acids, heavy metal salts, metallic oxides, mixtures of two or more of the foregoing, and soaps formed with the foregoing heavy metal salts or metallic oxides. The reaction is allowed to proceed until stirring the reaction mixture becomes difficult. Paraffin is then added to the reaction mixture with continued stirring of the reaction mixture. After completion of the reaction, excess fatty acids are distilled off using a high vacuum. The reaction mass is then cooled and a mixture of a) one or more fatty acids of Formula V: $R^4COOH$, where $R^4$ is a saturated or unsaturated, straight chain or branched (preferably straight chain) hydrocarbyl group of about 7 to 31 carbons, such as 13-17 carbons, preferably 15-17 carbons, and most preferably selected so that the compound of Formula V is stearic acid; and b) one or more anhydrous alkali metal salts selected from the group consisting of carbonates, bicarbonates and hydroxides where the alkali metal may be, for example, sodium, potassium or lithium, and wherein the preferred alkali metal salt is sodium hydroxide, is then added. The reaction melt may then be flaked, prilled, or, optionally, an aqueous dispersion may be made with the reaction melt produced by adding water to the reaction melt or adding the reaction melt to water at neutral pH to form a pumpable material of high active substance and low residual fatty acid content having excellent color and low odor.

DETAILED DESCRIPTION OF THE INVENTION AND DESCRIPTION OF THE PREFERRED EMBODIMENTS

This invention comprises a process for the manufacture of esters of Formula I by direct esterification of fatty acids of Formula II with salts of hydroxyalkanesulfonic acids of Formula III. Aqueous solutions or dried powders of the salts of the hydroxyalkanesulfonic acids may be used in the synthesis, which is carried out as a condensation reaction. The reaction is accomplished by mixing one or more fatty acids of Formula II with one or more salts of Formula III in a molar ratio in the range of from about 2.0:1.0 to about 1.0:1.0 of acid to salt, and more particularly in the range of from about 1.35:1.0 to about 1.1:1.0.

Examples of fatty acids suitable for use in this reaction include compounds of Formula II where R has the definition described above, and particularly where R has from 5 to 17 carbons. Even more particularly, R may be selected to form compounds of Formula II which are selected from the group consisting of coconut fatty acid ($C_5$–$C_{17}$); hydrogenated coconut fatty acid ($C_5$–$C_{17}$); oleic acid; capric acid ($C_9$); caprylic acid ($C_7$); lauric acid ($C_{11}$); palmitic acid ($C_{15}$); myristic acid ($C_{13}$); single, double and triple press stearic acids ($C_{15}$–$C_{17}$); tallow fatty acid; hydrogenated tallow fatty acid; synthetic, odd-numbered-carbon acids such as heptanoic ($C_6$) and pelargonic acid ($C_8$); and mixtures of any of the foregoing, and where the C values in parentheses are for the "R" in Formula II. It is to be noted that one skilled in the art will be aware that the naturally occurring fatty acids may occur as glycerides in their natural form. Preferably, coconut fatty acid is used.

Those skilled in the art will also appreciate that fatty acids which are obtained from a naturally occurring source are mixtures of acids having carbon chains of various numbers. Fatty acids made through synthetic routes may be made as chains of a single length, or various synthetic fatty acids may be mixed together to get a selected distribution of chain lengths for a particular product. It is within the scope of this invention to use one or more naturally occurring fatty acids (including mixtures thereof), synthetic fatty acids (including mixtures thereof) and mixtures of both natural and synthetic fatty acids.

Salts of hydroxyalkanesulfonic acids which are useful in the method of this invention are those of Formula III described above. Examples of salts of hydroxyalkanesulfonic acids of Formula III which are particularly useful in this reaction include those in which $R^1 =$ —$CH_2CH_2$—, —$(CH_2)_3$—, or —$CH_2CH(CH_3)$—; and X=sodium, potassium, lithium or ammonium; these include, for example, sodium hydroxyethane sulfonate (also called sodium isethionate), potassium methylisethionate, sodium dimethylisethionate, sodium 3-hydroxypropane-sulfonate, and potassium phenyl isethionate. For salts of Formula III, X is preferably selected to be sodium. This is due mostly to its commercial abundance.

The reaction is done in the presence of a catalyst. The catalyst is selected from the group consisting of:

a) one or more alkanesulfonic acids and hydroxyalkane-sulfonic acids of Formula IV: $R^2SO_3H$, where $R^2$ is selected from the group consisting of straight chain and branched saturated alkyls having from 1 to 4 carbons (for example, methyl, ethyl, propyl and butyl), and straight chain and branched saturated hydroxyalkyls of 2 to 4 carbons having one hydroxyl group where the hydroxyl group can be anywhere on the $R^2$ chain (for example, 2-hydroxyethyl, 2-hydroxypropyl and 3-hydroxybutyl). (More particular examples of suitable values for $R^2$ include $CH_3$—, $CH_3CH_2$— and $HOCH_2CH_2$—);

b) one or more aryl sulfonic acids of Formula VI: $R^3SO_3H$, where $R^3$ is selected from the group consisting of phenyl and tolyl;

c) one or more inorganic acids selected from the group consisting of sulfuric acid, phosphoric acid, hypophosphoric acid and boric acid and anhydrides of the foregoing acids;

d) one or more heavy metal salts selected from the group consisting of zinc sulfate, zirconium sulfate, zinc isethionate, aluminum sulfate, stannous sulfate, titanium sulfate, cadmium sulfate, tungsten phosphate and zinc borate;

e) one or more metallic oxides selected from the group consisting of zinc oxide, aluminum oxide, magnesium oxide, cerium oxide, didymium oxide, zirconium oxide and lanthanium oxide;

f) mixtures of two or more of the materials listed in a), b), c), d) and e); and g) soaps formed with the heavy metal or metallic oxides listed in d) and e).

The catalyst should be used in an amount of from about 0.05 to about 1.0 percent by weight of the initial reaction mass, and preferably from 0.05 to about 0.3 percent. Mixtures of catalysts may also be used. Zinc oxide as a single catalyst is used for a particularly efficient process, but other catalysts may be selected on the basis of properties desired in the final product or decomposition temperature of the catalyst.

The fatty acid (which may be a single acid or a mixture of acids) and the salt of the hydroxyalkanesulfonic acid (which may be a single salt or a mixture of salts) are mixed together with a selected catalyst in a vessel of appropriate size at atmospheric pressure fitted with an agitator (such as a 20 horsepower, two-speed drive with anchor agitator or equivalent), a subsurface nitrogen purge line and vacuum distillation piping with appropriately sized heat exchangers and vacuum receivers. For the examples in this application, a 5000 gallon (18,925 liters) or more (preferably 20 m$^3$) stainless steel stirred batch reactor was used. The reactor may be made of 316 stainless steel and designed to withstand pressures from 215 pound per square inch (gauge (14.6 bar) to full vacuum at a temperature of 650 degrees F. (343 degrees C.).

The direct esterification is carried out by heating the mixture with agitation so that the temperature of the mixture is elevated to a temperature of from about 180 degrees to about 240 degrees C., preferably in the range of from about 190 degrees to about 200 degrees C., and most preferably in the range of from about 195 degrees to about 198 degrees C. Once the mixture reaches the desired temperature, the reaction is allowed to continue toward completion. The times may vary considerably depending on reaction temperature and amount of catalyst; under the preferred experimental conditions described herein the times are on the order of 10–12 hours.

During the esterification procedure water is produced. This water is removed by distillation from the reaction mass using a subsurface purge of an inert gas, preferably nitrogen. An inert gas inhibits oxidation reactions of the reaction mixture. Such oxidation promotes poor color and odor properties. The inert gas also acts as a carrier gas and aids the removal of water during distillation.

The progress of the esterification reaction is followed analytically by titrimetric and gas chromatographic analyses well known by those skilled in the art to track the decrease in fatty acid content of the mixture and the increase in the amount of ester (for example, sodium acylisethionate) formed as the reaction progresses toward completion. (For examples of such analytical techniques see *Detergent Analysis-A Handbook for Cost-Effective Quality Control*, by B. M. Milwidsky and D. M. Gabriel (George Goodwin, London 1982) incorporated by reference herein in its entirety), especially at pages 119–120, 133–134 and 255.

Suitable esters formed during the course of a typical reaction include sodium cocoyl isethionate (SCI), where R=$C_7$–$C_{17}$, $R^1$=—$CH_2CH_2$— and X=Na.

During the course of the esterification, the reaction mass becomes exceedingly viscous, thus slowing the water distillation process and essentially stopping the condensation. At this point (which occurs, for example, when the activity of sodium cocoyl isethionate (SCI) is at about 60–70 percent activity, such as 60 percent activity), paraffin wax is added in an amount of from about 1 to about 50 weight percent of the reaction mass. More particular values for the amount of paraffin used is from about 5 to 30 weight percent with a range of from about 10 to about 15 weight percent being preferred.

It is to be noted that the activity of SCI is measured as the amount of SCI which is actually present in the reaction mixture as determined by titrimetric analysis as described above. The paraffin wax used here is of the type commonly defined as paraffin wax: a white, translucent, tasteless, odorless solid consisting of a mixture of solid hydrocarbons of high molecular weight, for example, $C_{36}H_{74}$. Paraffin waxes are soluble in benzene, ligroin, warm alcohol, chloroform, turpentine, carbon disulfide, and olive oil and insoluble in water and acids. (See the definition of paraffin wax in *Hawley's Condensed Chemical Dictionary* (11th Edition 1987). The addition of the paraffin wax lowers the viscosity so that complete condensation can be achieved. Particular types of paraffin wax which may be used with the method of this invention include synthetic and natural waxes, particularly refined paraffin waxes, and more particularly, refined paraffin waxes having a Chemical Abstracts' Service (CAS) Registry Number 64742-51-4. This type of refined paraffin wax has a melting point of 52–72 degrees C., low Saybolt color (as evaluated using the American Society for Testing and Manufacturing standard D-156 (ASTM Designation D 156-87), incorporated by reference herein in its entirety) (+28 minimum, where +30 is the lightest), and a kinematic viscosity of 3–8 centistokes at 99 degrees C. (as measured by using American Society for Testing and Manufacturing standard D-445, incorporated by reference herein in its entirety) or a similar method. While a wide variety of temperatures for the paraffin may be used, it has been found convenient to have the paraffin added to the reaction mixture in the range of from 60 to 90 degrees C., such as about 75 degrees C. The paraffin may be metered into the reaction mixture and is preferably added at such a rate that the temperature of the reaction mixture is maintained in the desired range.

The course of the reaction is followed using the same methods as described above until no further condensation (or substantially no further condensation) can be achieved. At this point, a vacuum is slowly applied to the reaction vessel, while the reaction mass is at a temperature of between 180 degrees and 240 degrees C., preferably between 190–200 degrees C., and most preferably between 195–198 degrees C., to distill off excess fatty acids. It is preferred that the vacuum not be applied too early. The vacuum should be applied so that the foam can be controlled. The agitation should be adjusted so that the stirring action does not sling the reactor contents. For the vessels described in the Examples, a stirring rate of about 30–40 revolutions per minute (rpm) is satisfactory.

The vacuum is slowly increased and the pressure is slowly lowered to less that 80 millimeters of mercury absolute, such as 50 millimeters of mercury absolute, more particularly less than 10 millimeters of mercury absolute and preferably less than 5 millimeters of mercury absolute, with less than 4 millimeters of mercury absolute being more preferable. The distillation is stopped once the residual fatty acids content in the reaction mass is determined to be less than 15 weight percent, preferably less than 5 weight percent, and most preferably less than 3 weight percent. The fatty acids distilled off may be recovered and recycled back into subsequent production. The addition of the paraffin wax essentially lowers the melting points of the products produced by this process so that the melt is still a fluid at temperatures below 140 degrees C. The degree of conversion is very good. For example, the conversion of the sodium isethionate using this method has reached greater than 90 percent using zinc oxide.

The fatty acid content (for example, coconut fatty acid content) is monitored by measuring acid number.

The reaction mass is then cooled, preferably to a temperature below 180 degrees C., and most preferably to a temperature below 150 degrees C. To the cooled reaction mass is added a mixture of: a) one or more fatty acids of Formula V where the fatty acid is preferably selected to be stearic acid, for example triple press stearic acid; and b) one or more anhydrous alkali metal salts selected from the group consisting of carbonates, bicarbonates and hydroxides where the alkali metal may be, for example, sodium, potassium or lithium, and wherein the preferred alkali metal salt is sodium hydroxide. The addition of these fatty acids further depresses the freezing point so that the material is a fluid at temperatures down to 50 degrees C. The addition of anhydrous alkali metal salt is believed to be essential to limit transesterification of the added fatty acids with the acyl group of the reaction product.

In order to make a pumpable fluid (pumpable down to 50 degrees C.), the mixture of the reaction product, fatty acids and alkali metal salt must be combined with a diluent such as water. It is essential that prior to the introduction of water into the system, the pH of the mixture of the reaction product, fatty acids and alkali salt be near neutral, preferably in the pH range of 6–7. The near neutral reaction melt is then diluted into water using water in an amount of from about 25 to about 90 weight percent of the melt, and preferably from about 30 to about 50 weight percent of the melt. The water may be at various temperatures, however, temperatures approaching the freezing point of water, such as 5–10 degrees C. are preferred in order to limit the hydrolysis of the active material in the mixture when water is added. Alternatively, the water may be added to the mixture using the amounts described above. The temperature at which the water and mixture are combined is critical to limiting the hydrolysis of the active material. Temperatures below 100 degrees C. are essential. Preferably the temperature is kept below 65 degrees C., and most preferably the temperature is kept below 50 degrees C. The pumpable fluid thus formed is an excellent composition which may be used for the production of personal care products, particularly, but not limited to, bar and liquid soaps.

EXAMPLES

The following nonlimiting examples are illustrative of the invention but should not be construed as limitations thereon. In the Examples, as well as elsewhere in this application, the chemical and scientific symbols have their usual meanings and all percents are weight percent unless otherwise specified.

Example 1

A 5000 gallon stainless steel stirred batch reactor equipped with a high performance agitator, a subsurface nitrogen purge line, and vacuum distillation piping with appropriately sized heat exchangers and vacuum receivers was charged with sodium hydroxyethane sulfonic acid solution (9130 pounds, 4150 kilograms) (Hostapon ® sodium isethionate solution from Hoechst Celanese Corporation, Somerville, N.J.) having 54 percent solids and 52.4 percent purity (verified by High Pressure Chromatographic Analyses) and having a color rating of Color 5 (based on American Public Health Association (APHA) rating system described at page 199 of the *Detergent Analysis Handbook* cited above and incorporated by reference in its entirety herein); pulverized French Process zinc oxide (25 pounds, 11.36 kilograms) and coconut fatty acid (8250 pounds, 3750 kilograms). A typical distribution of carbon chains in weight percent as determined by gas chromatography for the type of coconut fatty acid used in the process of this Example is: $C_6=0.4$; $C_8=7.6$; $C_{10}=6.5$; $C_{12}=47.7$; $C_{14}=18.4$; $C_{16}=8.9$; $C_{18}=6.2$; $C_{18}$ with 1 double bond$=3.7$; $C_{18}$ with 2 double bonds$=0.2$. This mixture was heated to 195 degrees C. as quickly as possible (about 6 hours) at atmospheric pressure with a subsurface nitrogen purge at a flow rate of about 16 standard cubic feet per minute (SCFM). Distillation of water from the reaction vessel was started when the temperature of the reaction mixture reached about 105 degrees C. at atmospheric pressure. Water from the incoming sodium hydroxyethane sulfonic acid solution was distilled off first with traces of fatty acids. After this water was distilled off, the water from the esterification process began to distill off. After 8 hours at 195 degrees C., the rate of distillation slowed and molten paraffin (about 120 degrees C.) (about 1700 pounds, 772.7 kilograms) having a mean carbon chain length of about 35 and a melting point of about 70 degrees C. was added. The reaction mass was then held for an additional two hours at 195 degrees C. at atmospheric pressure to complete the condensation. Next, the subsurface nitrogen purge was reduced to 2-3 SCFM while vacuum was slowly applied to reduce the pressure down to 4 millimeters of mercury absolute. Excess fatty acids were removed by vacuum distillation until the residual fatty acids were determined to be less than 5 percent by weight of the reactor contents. Residual fatty acid content was monitored by colorimetric assay for acid number, for example, as described in the *Detergent Analysis* reference cited above and incorporated by reference herein, at page 133. The reaction mass was then cooled to a temperature of about 150 degrees C. under about 200 millimeters of mercury absolute. After the reaction mass was cooled to 150 degrees C., triple pressed stearic acid (1485 pounds, 675 kilograms) and sodium hydroxide prills (11 pounds, 5 kilograms) were added simultaneously to the reaction vessel with stirring. The pH of the material in the reaction vessel was about 5.8-6.5 as measured at 10 percent solids in water. The pH was monitored by taking samples of the reaction mass at periodic intervals, diluting the samples to 10 percent solids by weight with distilled water and measuring the pH on a pH meter (Orion Research Model 501). Cooling of the contents of the reaction vessel was continued until the temperature reached 100 degrees C. At this point, ice water (9100 pounds, 4136.4 kilograms) was added as quickly as possible to the reaction vessel with stirring. The temperature of the material in the reaction vessel dropped to 65-70 degrees C. The reaction yielded 24,000 pounds (10,909 kilograms) of a white pumpable fluid containing 36 weight percent sodium cocoylisethionate as the active ingredient as determined by the two phase methylene blue titration procedure for anionic surfactants as described in Epton, S. R., "Method of Analysis for Certain Surface Active Agents", *Nature*, Volume 160, page 795 (1947) and incorporated by reference herein. Greater than 90 percent conversion of the sodium isethionate was achieved. Hydrolysis with the water addition was limited to 5 percent. Approximately 400 pounds (181.8 kilograms) of fatty acids were distilled off with the water at atmospheric pressure, and about 1200 pounds (545.5 kilograms) of fatty acids were distilled off using vacuum. Each of these distilled fatty acid fractions may be recycled into subsequent production. The process described in Example 1 was repeated three times and gave an average yield of 24,000 pounds (10,909 kilograms).

Example 2

The reaction described in Example 1 was repeated except that the initial charge to the reaction vessel was 1200 pounds (545.5 kilograms) of vacuum distilled fatty acids produced as by-product in Example 1 and 7050 pounds (3204.5 kilograms) of coconut fatty acid instead of the 8250 pounds of coconut fatty acid used in Example 1. The yield was about 24,000 pounds (10,909 kilograms) of a white pumpable fluid containing 36 weight percent sodium cocoyl isethionate (assuming a molecular weight of 336) as an active ingredient as determined by the two phase methylene blue titration procedure for anionic surfactants described above. Approximately 400 pounds (181.8 kilograms) of fatty acids were distilled off with the water at atmospheric pressure, and about 1200 pounds (545.5 kilograms) of fatty acids were distilled off using vacuum. Each of these distilled fatty acid fractions may be recycled into subsequent production. The process described in Example 2 was repeated three times to give an average yield of 24,000 pounds (10,909 kilograms) with an average of 36 percent activity. Greater than 90 percent conversion of the sodium isethionate was achieved. Hydrolysis with the water addition was limited to 5 percent.

Example 3

The reaction described in Example 1 was repeated except that the initial charge to the reaction vessel was 1200 pounds (545.5 kilograms) of vacuum distilled fatty acids produced as by-products in Example 1, 6650 pounds (3022.7 kilograms) of coconut fatty acid of the type described in Example 1, and 400 pounds (181.8 kilograms) of fatty acids that co-distilled with water as described in Example 1 instead of the 8250 pounds of coconut fatty acid used in Example 1. The yield was about 24,000 pounds (10,909 kilograms) of a white pumpable fluid containing 36 weight percent sodium cocoylisethionate as an active ingredient as determined by the two phase methylene blue titration procedure for anionic surfactants described above. Approximately 400 pounds (181.8 kilograms) of fatty acids were distilled off with the water at atmospheric pressure, and about 1200 pounds (545.5 kilograms) of fatty acids were distilled off using vacuum. Each of these distilled fatty acid fractions may be recycled into subsequent production. The yield for this example was the same as for Example 2; however, the addition of the distilled fatty acids skewed the carbon chain distribution of surfactant so that the proportion of $C_8$, $C_{10}$ and $C_{12}$ carbon chain length materials were increased. The process described in Example 3 was repeated five times to give an average yield per run of 24,000 pounds (10,909 kilograms) with an average activity of 37 percent. Greater than 90 percent conversion of the sodium isethionate was achieved.

Example 4

The process of Example 1 was followed except that methane sulfonic acid solution (99 pounds, 45 kilograms of 70 percent methane sulfonic acid) was used instead of zinc oxide. The yield was 24,000 pounds (10,909 kilograms), having an activity of 36.5 percent.

Example 5

The process of Example 4 was repeated except that para-toluene sulfonic acid (99 pounds, 45 kilograms of crystals having approximately 100 percent purity) was used instead of methane sulfonic acid. The yield was 24,000 pounds (10,909 kilograms), having an average activity of 37.5 percent.

Example 6

The process of Example 5 was followed except that hypophosphorous acid (72 pounds, 32.7 kilograms of a 50 percent solution) was added with the para-toluene sulfonic acid (99 pounds, 45 kilograms). The yield was 24,000 pounds (10,909 kilograms), having an activity of 36.0 percent.

Example 7

A 2 liter reaction vessel equipped with a subsurface nitrogen purge line, thermometer, distilling head (condenser and receiver) and a mechanical agitator was charged with sodium hydroxyethane sulfonic acid solution (410 grams, of the same type of Hostapon ® sodium isethionate as described in Example 1), pulverized French Process zinc oxide (1.1 gram), and lauric acid (345 grams, of 98% pure material as determined by gas chromatography). This mixture was heated to 195 degrees C. (about 2 hours) at atmospheric pressure with a subsurface nitrogen purge at a flow rate of about 15 liters per hour. After 7 hours at 195 degrees C., the distillation rate of the esterification water slowed and paraffin (71 grams of the same type of paraffin as described in Example 1) was added. The reaction mass was then held for an additional 2 hours at 195 degrees C. to complete the condensation. Next, excess fatty acid was removed by vacuum distillation (pressure was about 8 millimeters of mercury absolute) until the residual fatty acid was determined to be 6 percent by weight of the reactor contents. The reaction mass was then cooled to a temperature of about 160 degrees C. under nitrogen at atmospheric pressure. At this temperature stearic acid (62 grams) and sodium hydroxide prills (1 gram) were added simultaneously to the reaction vessel with stirring. The pH of the material in the reaction vessel was about 6.3 as measured at 10 percent solids in distilled water. This material was cooled down and bottled. The yield was about 625 grams and contained 69 weight percent sodium lauroylisethionate as the active ingredient. Greater than 90 percent conversion of the sodium isethionate was achieved. Totally, about 40 grams of lauric acid was distilled off with the water at atmospheric pressure and during the vacuum stripping phase. This distilled lauric acid may be recycled to subsequent production. The product had about 69 percent activity.

Example 8

The reaction described in Example 7 was repeated except that a stripped, hydrogenated coconut fatty acid (380 grams) was used instead of the lauric acid. The typical distribution of carbon chains in weight percent as determined for this type of coconut fatty acid is: $C_{10}=2$; $C_{12}=52$; $C_{14}=22$; $C_{16}=12$; $C_{18}=12$. The average acid number is 250–260. The reaction yielded 650 grams of a white material containing 70 percent by weight sodium cocoyl isethionate as the active ingredient. Greater than 90 percent conversion of the sodium isethionate was achieved. Approximately 45 grams of fatty acid were removed by distillation.

What is claimed is:

1. A process for making salts of acylisethionates of Formula I:

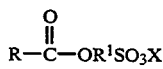

wherein:
R is selected from the group consisting of
A) saturated straight chain hydrocarbyl groups having from about 5 to about 31 carbons;
B) unsaturated straight chain hydrocarbyl groups having from about 5 to about 31 carbons and containing one unsaturation;
C) saturated branched chain hydrocarbyl groups having from about 5 to about 31 carbons; and
D) unsaturated branched chain hydrocarbyl groups having from about 5 to about 31 carbons and containing one unsaturation;

$R^1$ is a saturated or unsaturated straight chain $C_2$–$C_4$ hydrocarbyl group selected from the group consisting of ethylene, propylene and butylene; and X is selected from the group consisting of sodium, potassium, lithium and ammonium; and wherein:
1) said method comprises a direct esterification of at least one fatty acid of Formula II: RCOOH, with at least one hydroxyalkanesulfonic acid salt of Formula III: $HOR^1SO_3X$, where R, $R^1$, and X have the same meanings as defined for Formula I, and wherein the ratio of said fatty acid of Formula II to the salt of Formula III is from about 2.0:1.0 to about 1.0:1.0;
2) said direct esterification is done at a temperature between about 180 degrees and 240 degrees C. in the presence of from about 0.05 to about 1.0 percent by weight of the initial reaction mass of a catalyst selected from the group consisting of at least one member of the group consisting of:
   a) one or more alkane sulfonic acids and hydroxyalkanesulfonic acids of Formula IV: $R^2SO_3H$, where $R^2$ is selected from the group consisting of straight chain and branched saturated alkyls having from 1 to 4 carbons, and straight chain and branched saturated hydroxyalkyls of 2 to 4 carbons having one hydroxyl group where the hydroxyl group can be anywhere on the $R^2$ chain;
   b) one or more aryl sulfonic acids of Formula VI: $R^3SO_3H$, where $R^3$ is selected from the group consisting of phenyl and tolyl;
   c) one or more inorganic acids selected from the group consisting of sulfuric acid, phosphoric acid, hypophosphoric acid and boric acid and anhydrides of the foregoing acids;
   d) one or more heavy metal salts selected from the group consisting of zinc sulfate, zirconium sulfate, zinc isethionate, zinc borate, aluminum sulfate, stannous sulfate, titanium sulfate, cadmium sulfate and tungsten phosphate;
   e) one or more metallic oxides selected from the group consisting of zinc oxide, aluminum oxide, magnesium oxide, cerium oxide, didymium oxide, zirconium oxide and lanthanium oxide;
   f) mixtures of two or more of the catalysts selected from the group comprising the catalysts listed in groups a), b), c), d) and e); and
   g) soaps formed with said heavy metal or said metallic oxides;
3) allowing the reaction to proceed toward completion while maintaining said temperature and removing water from said reaction mixture;
4) adding paraffin wax to said reaction mixture after the condensation reaction has substantially ceased;
5) resuming said reaction until no further condensation can be achieved under the reaction conditions;

6) slowly lowering the pressure in the reaction vessel containing said reaction mass at an initial temperature between 180 degrees and 240 degrees C. to less than 80 millimeters of mercury absolute and agitating said reaction mass so that the foam is kept to a minimum;

7) distilling off fatty acids from the reaction mass until the fatty acid content of said reaction mass is less than 15 weight percent;

8) cooling said reaction mass to a temperature below 180 degrees C.;

9) adding to said cooled reaction mass a mixture of:
   a) one or more fatty acids of Formula V: $R^4COOH$, where $R^4$ is a saturated or unsaturated alkyl group of 7 to 31 carbons; and
   b) one or more anhydrous alkali metal salts selected from the group consisting of carbonates, bicarbonates and hydroxides where the alkali metal is selected from the group consisting of sodium, potassium and lithium.

2. The method as claimed in claim 1 comprising the further steps of mixing water with said cooled reaction mass and forming a pumpable fluid.

3. The method as claimed in claim 1 wherein $R^1$ is ethylene.

4. The method as claimed in claim 1 wherein said direct esterification is done at a temperature below 200 degrees C.

5. The method as claimed in claim 1 wherein X is sodium.

6. The method as claimed in claim 1 wherein $R^4$ is a straight chain hydrocarbyl group.

7. The method as claimed in claim 6 wherein $R^4$ has 13 to 17 carbons.

8. The method as claimed in claim 6 wherein $R^4$ has 15 to 17 carbons.

9. The method as claimed in claim 1 wherein the compound of Formula V is selected to be stearic acid.

10. The method as claimed in claim 1 wherein R is selected to form compounds of Formula II wherein the compounds of Formula II are selected from the group consisting of coconut fatty acid; hydrogenated coconut fatty acid; oleic acid; capric acid; caprylic acid; lauric acid; palmitic acid; myristic acid; single, double and triple press stearic acids; tallow fatty acid; hydrogenated tallow fatty acid; heptanoic acid, pelargonic acid; and mixtures of the foregoing acids.

11. The method as claimed in claim 1 wherein $R^1 = -CH_2CH_2-$, $-(CH_2)_3-$, or $-CH_2CH(CH_3)-$.

12. The method as claimed in claim 1 wherein the compound of Formula III is selected from the group consisting of sodium hydroxyethane sulfonate, potassium methylisethionate, sodium dimethylisethionate, sodium 3-hydroxypropanesulfonate, and potassium phenyl isethionate.

13. A process as claimed in claim 1 for making salts of acylisethionates of Formula I:

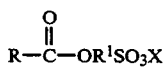

wherein:
R is selected from the group consisting of
A) saturated straight chain hydrocarbyl groups having from 5-17 carbons; and
B) unsaturated straight chain hydrocarbyl groups having from from 5-17 carbons and containing one unsaturation;

$R^1$ is ethylene;

X is sodium; and wherein:
1) said method comprises a direct esterification of at least one fatty acid of Formula II: RCOOH, with at least one hydroxyalkanesulfonic acid salt of Formula III: $HOR^1SO_3X$, where R, $R^1$, and X have the same meanings as defined for Formula I, and wherein the ratio of said fatty acid of Formula II to the salt of Formula III is about 1.0:1.0;

2) said direct esterification is done at a temperature between about 180 degrees and 240 degrees C. in the presence of from about 0.05 to about 1.0 percent by weight of the initial reaction mass of a catalyst selected from the group consisting of at least one member of the group consisting of:
   a) one or more alkane sulfonic acids and hydroxyalkanesulfonic acids of Formula IV: $R^2SO_3H$, where $R^2$ is selected from the group consisting of $CH_3-$, $CH_3CH_2-$ and $HOCH_2CH_2-$;
   b) at least one aryl sulfonic acid of Formula VI: $R^3SO_3H$, where $R^3$ is selected from the group consisting of phenyl and tolyl;
   c) at least one heavy metal salt selected from the group consisting of zinc sulfate and zinc isethionate;
   d) zinc oxide;
   e) mixtures of at least two catalysts selected from the group comprising a), b), c) and d); and
   f) soaps formed with c) or d);

3) allowing the reaction to proceed toward completion while maintaining said temperature and removing water from said reaction mixture;

4) adding paraffin wax to said reaction mixture after the condensation reaction has substantially ceased;

5) resuming said reaction until no further condensation can be achieved under the reaction conditions;

6) slowly lowering the pressure in the reaction vessel containing said reaction mass at an initial temperature between 180 degrees and 240 degrees C. to less than 80 millimeters of mercury absolute and agitating said reaction mass so that the foam is kept to a minimum;

7) distilling off fatty acids from the reaction mass until the fatty acid content of said reaction mass is less than 15 weight percent;

8) cooling said reaction mass to a temperature below 180 degrees C.;

9) adding to said cooled reaction mass a mixture of:
   a) one or more fatty acids of Formula V: $R^4COOH$, where $R^4$ is a saturated or unsaturated alkyl group of 7 to 31 carbons; and
   b) one or more anhydrous alkali metal salts selected from the group consisting of carbonates, bicarbonate and hydroxides where the alkali metal is selected from the group consisting of sodium and potassium.

* * * * *